(12) United States Patent
Lee et al.

(10) Patent No.: US 9,839,746 B2
(45) Date of Patent: Dec. 12, 2017

(54) ELASTIC BAND POWERED FLUID DELIVERY APPARATUS

(71) Applicants: Freddie Eng Hwee Lee, Singapore (SG); Withawin Wongdee, Chon Buri (TH)

(72) Inventors: Freddie Eng Hwee Lee, Singapore (SG); Withawin Wongdee, Chon Buri (TH)

( * ) Notice: Subject to any disclaimer, the term of this patent is extended or adjusted under 35 U.S.C. 154(b) by 365 days.

(21) Appl. No.: 14/602,679

(22) Filed: Jan. 22, 2015

(65) Prior Publication Data

US 2015/0209506 A1    Jul. 30, 2015

Related U.S. Application Data

(60) Provisional application No. 61/931,219, filed on Jan. 24, 2014.

(51) Int. Cl.
| | | |
|---|---|---|
| *A61M 5/145* | (2006.01) | |
| *B65B 3/00* | (2006.01) | |
| *B65B 3/12* | (2006.01) | |
| *B65B 3/30* | (2006.01) | |
| *B65B 39/00* | (2006.01) | |

(52) U.S. Cl.
CPC ...... *A61M 5/14526* (2013.01); *A61M 5/1454* (2013.01); *A61M 5/1456* (2013.01); *A61M 5/14546* (2013.01); *B65B 3/003* (2013.01); *B65B 3/12* (2013.01); *B65B 3/30* (2013.01); *A61M 2205/0216* (2013.01); *A61M 2205/3341* (2013.01); *A61M 2209/045* (2013.01); *B65B 2039/009* (2013.01)

(58) Field of Classification Search
CPC .......... A61M 5/14526; A61M 5/14546; A61M 5/1454; A61M 5/1456; A61M 2039/009; A61M 2205/3341; A61M 2205/0216; A61M 2209/045; A61M 5/31555; A61M 5/2033; A61M 2005/2073; B65B 3/30; B65B 3/12; B65B 3/003; B65B 2039/009
See application file for complete search history.

(56) References Cited

U.S. PATENT DOCUMENTS

| | | |
|---|---|---|
| 5,743,879 A | 4/1998 | Kriesel |
| 5,800,405 A | 9/1998 | McPhee |
| 6,019,747 A | 2/2000 | McPhee |

(Continued)

*Primary Examiner* — Kevin C Sirmons
*Assistant Examiner* — Amber Stiles
(74) *Attorney, Agent, or Firm* — Wolf, Greenfield & Sacks, P.C.

(57) ABSTRACT

This invention relates to a fluid delivery apparatus, system and method, in particular the use of elastic bands to generate the force required to push fluid out from a container. The fluid that is delivered from the container maybe prefilled and stored prior to its actuation by the elastic band driver or it could be filled just before use. In one embodiment disclosed, a prefilled option would require the user to attach an appropriate extension tubing that acts as a flow control tube to the fluid container which in one embodiment is tubular shaped. In the application where the device is filled just before use, the fluid container that would be engaged with the actuating housing is presented with a fixed rate flow tube. The selection of a particular device configuration replaces the need for programming a flow rate into an electronic syringe pump.

16 Claims, 8 Drawing Sheets

(56) References Cited

U.S. PATENT DOCUMENTS

| | | |
|---|---|---|
| 6,348,043 B1 | 2/2002 | Hagen et al. |
| 6,712,794 B2 | 3/2004 | Kust et al. |
| 2003/0105430 A1* | 6/2003 | Lavi .................. A61M 5/2033 604/136 |
| 2004/0210199 A1 | 10/2004 | Atterbury et al. |

* cited by examiner

ELASTIC BAND POWERED FLUID DELIVERY APPARATUS

CROSS-REFERENCE TO RELATED APPLICATIONS

This application claims the benefit under 35 U.S.C. §119 (e) of U.S. Provisional Application Ser. No. 61/931,219, entitled "ELASTIC BAND POWERED FLUID DELIVERY DEVICE" filed on Jan. 24, 2014, the entire contents of which are incorporated herein by reference.

TECHNICAL FIELD

The present invention relates to a fluid delivery apparatus. In particular, it relates to a fluid delivery apparatus for infusion and injection of fluid medical substance.

BACKGROUND

The use of disposable elastomeric ambulatory infusion devices have gain wide acceptance due to its ease of use, safe and effective means of drug delivery in non hospital based settings.

The manufacture of such devices has been extremely challenging with respect to achieving accurate flow rates. The flow rates are primarily governed by the combined effect of the pressure generated when the device is filled and a flow control tube in accordance to Bernoulli's theorem. Depending on the extent of unevenness in the wall thickness of the fluid container, the filling of medication fluid into the fluid container may result in non uniform expansion in which lesser than intended extent of the surface area is effected in the force pushing the fluid. This complicates the process of matching flow tube to pressure which is critically important in order to produce accurate flow rates.

Another drawback resulting from the variation in pump pressure is that it makes simultaneously multiple filling impractical, as weaker pumps would fill up easily and end up with larger volume of medication than stronger pumps.

There are further limitations in the use of elastomeric pumps in situations where infusions are not required immediately after filling. For example, a patient may need multiple doses over a long duration. The filled delivery apparatuses that are used later may not have the intended flow rates as the pressure generated by the elastomer elements would typically change with time.

SUMMARY OF THE INVENTION

In the disclosed invention, possible hysteresis energy losses can be avoided in the fluid delivery apparatus and has no impact on performance change, as the actuator module is only engaged when infusion is ready to take place.

As the driving mechanism pushing the fluid is housed in a separate actuator module, it is not subject to any stress with the fluid container being filled with fluid. The filled fluid container could as a result be stored over an extended period covering the therapy duration, and be assembled to the actuator module only right before use, therefore the risks of changed performance of fluid medication delivery is reduced.

From a systems perspective, the disclosed invention could be presented as elements or components of workstations comprising filling process with fixed or variable fill volume selection, engagement of actuating module with the filled containers and synced label printing and dispensing that could be sequenced to the filling process to ensure positive matching of labels to device.

The present invention disclosed is both a system and device setup for fixed rate infusion of medicinal fluids in which the fluid container will be engaged into an actuator module by rotational motion executable by manual or machine assisted means.

The force generated by the stretched elastic bands within the actuating module is approximately constant throughout its lateral displacement such that intended fixed flow rates could be achieved regardless of varying volumes of the fluid remaining in the fluid container. This enables a common actuator module to function with different initial fill volumes of the container, giving great benefits in an infusion environment where the fixed rate fluid flow and intended medicinal dose may necessitate a uniquely specific infusion volume. Typically, this would require the need for a wide range of receptacle volumes and invariably actuator modules to achieve the intended medication dose. This disclosed invention is uniquely different from known devices where fluid is instantaneously injected instead of infused with a preset flow rate that requires a force profile that is operable over a range of fluid volumes.

Embodiments of the present invention allow combinations of elastic properties, shapes, dimensions and also different pre-stressing levels to cumulatively result in a desired force profile for fluid delivery with desired flow rate. The use of elastic bands offers significantly better force consistency as in a stretched band, it is linearly dependent on the draw length following Hooke's Law. This is uniquely different from that in a known elastomeric pump.

In one embodiment, the fluid delivery apparatus includes disc plates as coupling elements, and elastic bands strapped circumferentially around the disc plates in a parallel manner. An opening on one of the disc plates and an axial void surrounded by the fluid container could accommodate a piston or tubular shaped element that serves fittingly well as plungers to push fluid out from a fluid container or tubular receptacle. Such a structure is both simple yet advantages in reducing total size of the devices as the plunger recesses into the void of the fluid container as fluid is dispensed. The disc plates may be replaced with functionally similar means like discs with conical or dome shaped protrusions that slide coaxially through an opening in the adjacent plates.

In one embodiment, the plunger is an integral part of a stopper gasket disposed within the fluid container. Yet in other embodiments, the plunger could be detachable and becomes operable in causing the elastic bands to stretch only when it is attached to the fluid container, prior to engagement of the actuator module and the fluid container. It is also within the scope of this invention that the plunger is an element of one of the disc plates within the actuator housing and slidable coaxially within the void section of the other disc plate, causing the elastic bands to stretch when the fluid container is engaged to the housing of the actuator module.

BRIEF DESCRIPTION OF DRAWINGS

The preferred embodiment of this invention is explained by the figures, by way of sample only, in which:

FIG. 10 shows a fluid delivery apparatus of FIG. 1A in a typical infusion set up.

DETAILED DESCRIPTION OF PREFERRED EMBODIMENTS

This invention relates to a fluid delivery system, method and device, in particular the use of elastic bands to generate the force required to push fluid out from a container. In the context of medicinal fluids administration, the system disclosed could potentially offer an alternative to infusion means previously provided by electronic pumps or syringe drivers. The fluid that is delivered from the fluid container maybe prefilled and stored prior to its actuation by the elastic band driver or fluid container could be filled just before use.

In one embodiment disclosed, a prefilled option would require the user to attach an appropriate extension tubing that acts as a flow control tube to the fluid container which in one embodiment is tubular shaped. In the application where the device is filled just before use, the fluid container that would be engaged with the housing of the actuator module is presented with a fixed rate flow tube. The selection of a particular device configuration replaces the need for programming a flow rate into an electronic syringe pump.

An array of elastic bands, which may be fabricated from any stretchable material like isoprene, silicone or any elastomeric material, is used in embodiments of the present invention in the actuating module that produces a relatively constant force acting on the plunger of the fluid container when the device is being operated. One means making this possible is by pre stressing some of the elastic members so that the cumulative elastic stress versus strain profile of the final elastic band assembly presents a regressive portion in its elastic range due to the two different profiles being superimposed over each other. Pre stressing is achieved by subjecting some or all of the elastic members in the actuating module to a stretch even before the fluid container is attached. Another means is to configure the length of the plunger and/or the central protruding feature of the inner disc plate such that the elastic bands are stretched with engagement of the actuator module and the fluid container before any displacement of the plunger in the fluid container occurs.

When stretched, the combination of elastic bands that strap the circumference of the adjacent disc plates in an annular manner stores elastic potential energy. One of the disc plates within the actuator housing is configured to receive the end of the plunger of the fluid container such that engagement of the fluid container with the actuator housing will cause the adjacent disc plates to move outwardly from each other, to stretch the elastic bands. The housing has annular grooves on its inner wall that receives the screw thread on the outer circumferential rim of the fluid container, when the fluid container is rotationally inserted into the actuator housing. Upon opening the clamp that shuts off fluid communication between the device and patient, the stored elastic potential energy is released and converted to kinetic energy propelling the disc plate and the plunger that is in contact towards the distal end of the fluid container pushing out its content.

As potential energy is created by stretching elastic bands, there is no necessity for the drive mechanism to recess into the void of the fluid container created by the dispensed fluid.

Figure 1A:
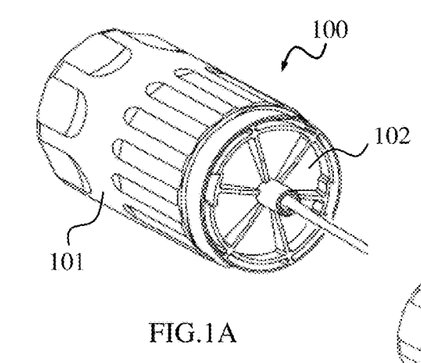
FIG. 1A is a perspective view showing a fluid delivery apparatus according to one embodiment of the present invention.
Figure 1B:
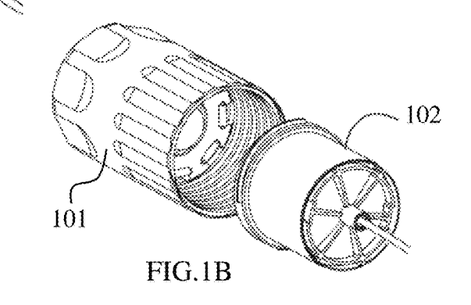
FIG. 1B is a perspective view showing the fluid delivery apparatus of FIG. 1A before the fluid container is attached to an actuator module.
Figure 1C:
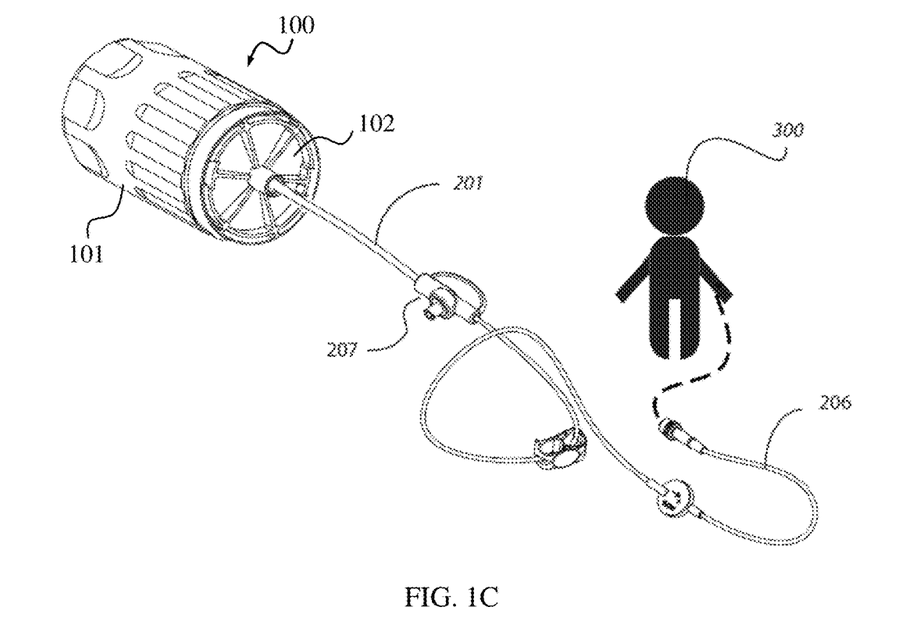

Referring to FIGS. 1A, 1B and 10, a fluid delivery apparatus 100 includes an actuator module 101 and a fluid container 102 which may be made and filled with fluid separately, and attached to housing 120 of actuator module 101 for the delivery of fluid, e.g. infusion of medication to patients.

Actuator module 101 provides a force to cause the fluid filled in the fluid container 102 to flow through the tubes 201 which connects to the vascular system of a patient 300 by means of a catheter. The flow restrictor 206 consist of a capillary of plastic or glass, is connected to the fluid container. The internal diameter and length of fluid restrictor 206 would determine the flow rate with a given pressure differential between the device and the patient's vascular pressure at the venipuncture site. This relationship is governed by Bernoulli's theorem, whereby some other factors affecting flow rate would be temperature and fluid viscosity. The fluid container maybe filled via an in-line fitting 207.

Figure 2:
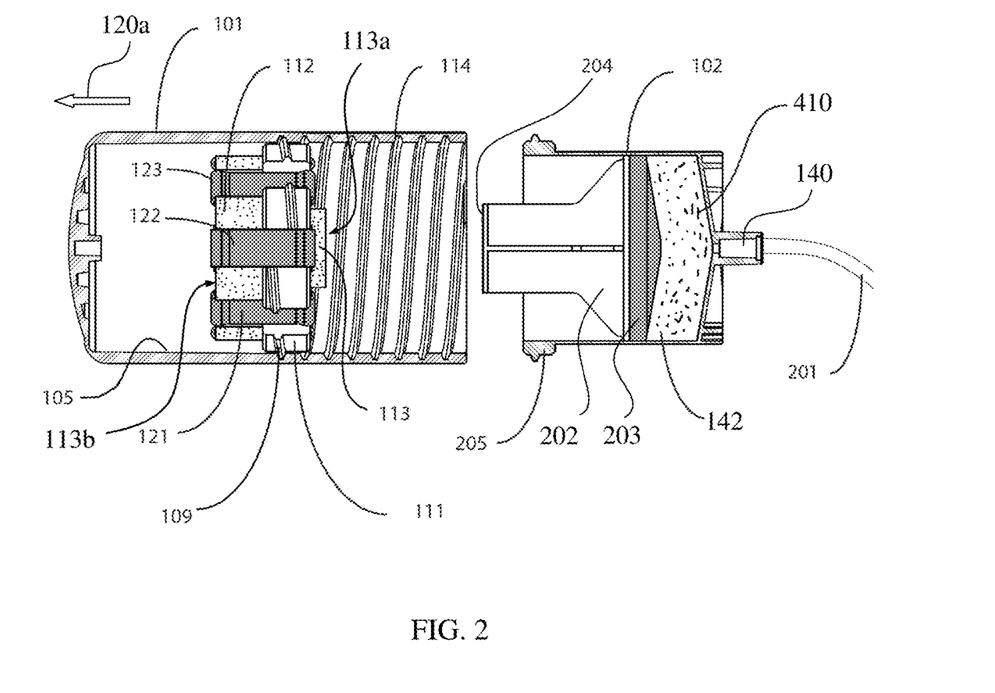
FIG. 2 is a cross sectional view of FIG. 1B.

In the embodiment disclosed, as shown in FIG. 2, fluid container 102 has a port 140 formed at one end through which a fluid 410 may be filled into and delivered from fluid container 102. A plunger 202 is movably disposed in fluid container 102 to form a chamber 142 between the plunger 202 and port 140 for containing the fluid 410. Actuator module 101 includes a support member e.g. a first disc plate 111 disposed in housing 120. An actuator including a second disc plate 112 and a protrusion 113 connected to second disc plate 112, is movably disposed through first disc plate 111. Protrusion 113 extends through a central opening 111a formed on first disc plate 111, such that a first end 113a of protrusion 113 of the actuator is disposed at one side of first disc plate 111. A second end 113b of second disc plate 112 of the actuator is disposed at an opposite side of first disc plate 111.

Fluid container 102 is generally tubular shaped. Plunger 202 has a plunger body e.g. shown in FIG. 3A in the form of a stopper gasket 203, disposed within fluid container 102. Plunger 202 has a base 204 that will come in contact with first end 113a of protrusion 113 of the actuator in housing 120, when fluid container 102 and housing 120 are engaged. The stopper gasket 203 of plunger 202 seals the fluid tightly within chamber 142 and ensures that during operation, fluid is pushed out towards the port 140 of the fluid container 102 without any leaks. (See FIG. 2)

Further referring to FIG. 2, the first and second disc plates 111 and 112 are connected and secured at second end 113b of disc plate 112, with a resilient member which, in this embodiment, includes elastic bands 121 to 128 (only elastic band 121, 122, 123 are shown in FIG. 2), such that displacing the disc plates 111, 112 away from each other will cause the elastic bands to stretch.

The inner walls 105 of housing 120 has thread grooves 114, that receives and engages the circumferential flange 205 of the fluid container 102 when fluid container 102 and housing 120 are engaged by rotational movements. The first disc plate 111 that is in closest proximity to the open end of the housing 120 has truncated screw thread 109 on its circumferential wall to accommodate the positions of the elastic bands 121 to 128. The screw threads 109 on disc plate 111 allow easy assembly and positioning of the first and second discs plates 111 and 112 into the housing 120 after disc plates 111, 112 are secured by the elastic bands (121~128). While the embodiment disclosed has eight strips or loops of elastic bands, it is understood that any other number of elastic bands would still be covered by this invention.

When fluid container 102 is filled with fluid and the fluid is sealed in the fluid container, and when the fluid container 102 is attached to housing 120, plunger 202 acts against first end 113a of protrusion 113 of the actuator, to stretch the elastic bands 121 to 128 along a longitudinal direction 120a of housing 120, to store elastic potential energy in the elastic bands. When port 140 is opened, the elastic potential energy is released, such that the elastic bands shrink to drive the actuator to push the plunger 202 toward port 140, to eject the fluid out of chamber 142 from port 140.

The fluid may be pre-filled into chamber 142, before the fluid container 102 is attached to housing 120 to stretch the elastic bands. Alternatively, the fluid may also be filled when the fluid container is attached to housing 120 and to stretch the elastic bands.

The base 204 of the plunger 202 may be presented with features that matches the receiving end of the protrusion 113, for example a concave end profile for the protrusion 113 to match a curved convex features terminating the end of the plunger 204 which will accommodate the rotational action of the fluid container 102.

In the instance where protrusion 113 contacts base 204 of plunger 202 and forms a connected unitarily movable element before flange 205 reaches its end position along grooves 114, further advancement of fluid container 102 toward the actuator will cause a pre-stressing of elastic bands 121 to 128. This pre stressing produces a force acting on plunger 202 and the stopper gasket 203 even though fluid container 102 is unfilled. The effect of pre stressing is to extend the regressive range of the force profile acting on the fluid. The pre stressing of the force just prior to use is a major advantage because it avoids the loss of energy and difficult-to-predict hysteresis losses in the elastic bands.

To achieve pre stressing by aforesaid described means, protrusion 113 could be made longer as it is a better option than increasing the length of plunger 202 if it is necessary to present a compact fluid container.

If the goal is to enable filling of the fluid container by retraction of plunger 202 instead of the disclosed embodiment where filling is via the inline fill fitting 207, then a longer plunger would be more user friendly.

Figure 3A:
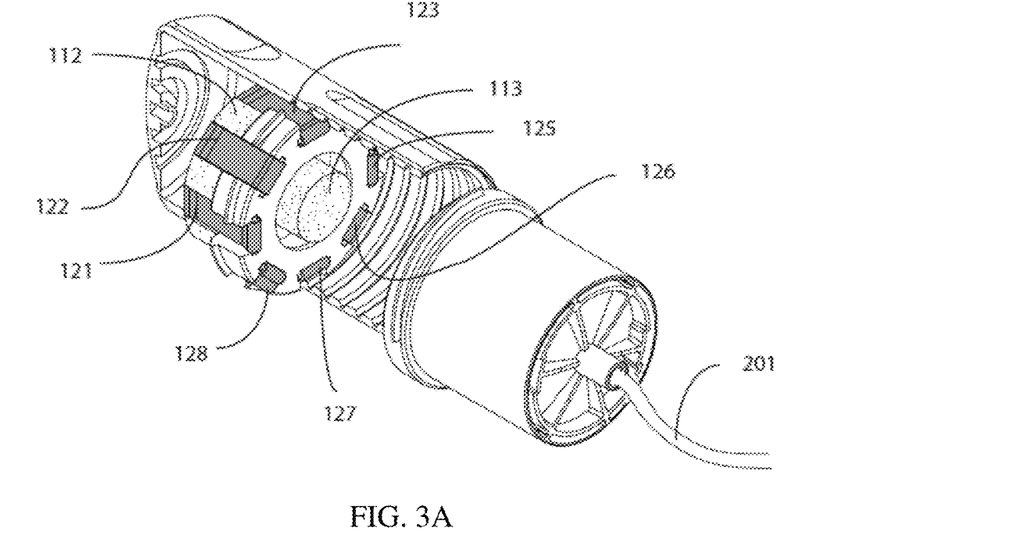
FIG. 3A and FIG. 3B are perspective views of FIG. 1B with cut out sections of the fluid container and actuator module showing the elastic bands securing the disc plates.
Figure 3B:
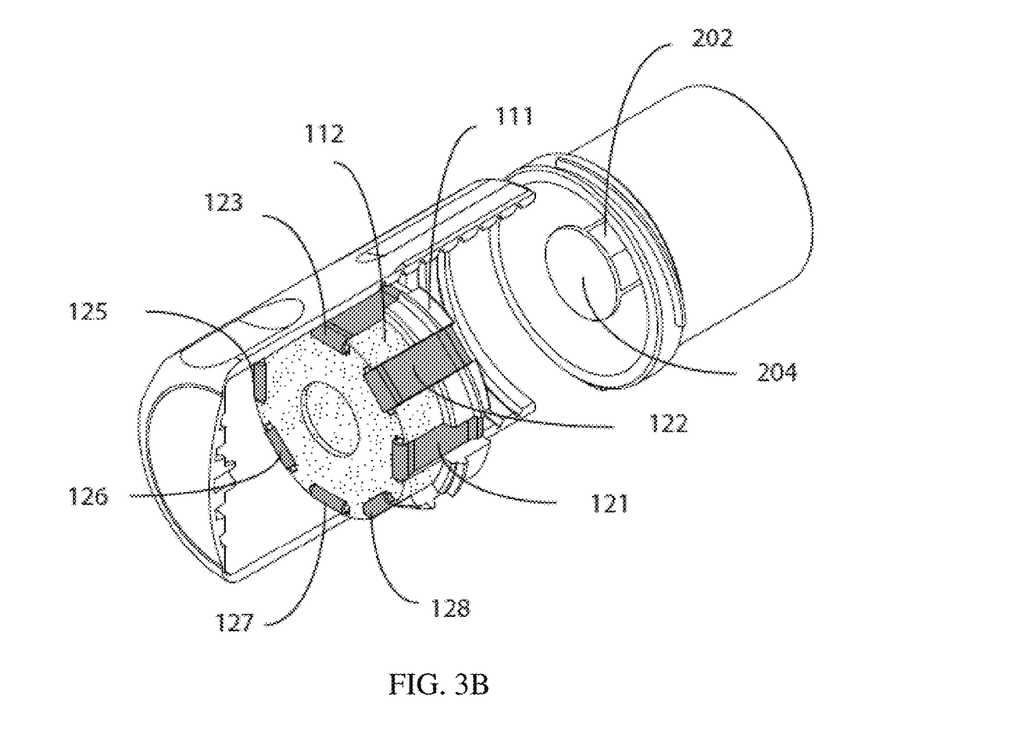

Referring to FIG. 3A and FIG. 3B, the embodiment has eight elastic bands labelled 121 through 128, disposed along a circumference of first disc plate 111, and connect first disc plate 111 and second disc plate 112 in parallel. While the embodiment disclosed has right strips or loops of elastic bands, it is appreciated that any other number of elastic bands would still be covered by this invention.

Figure 4A:
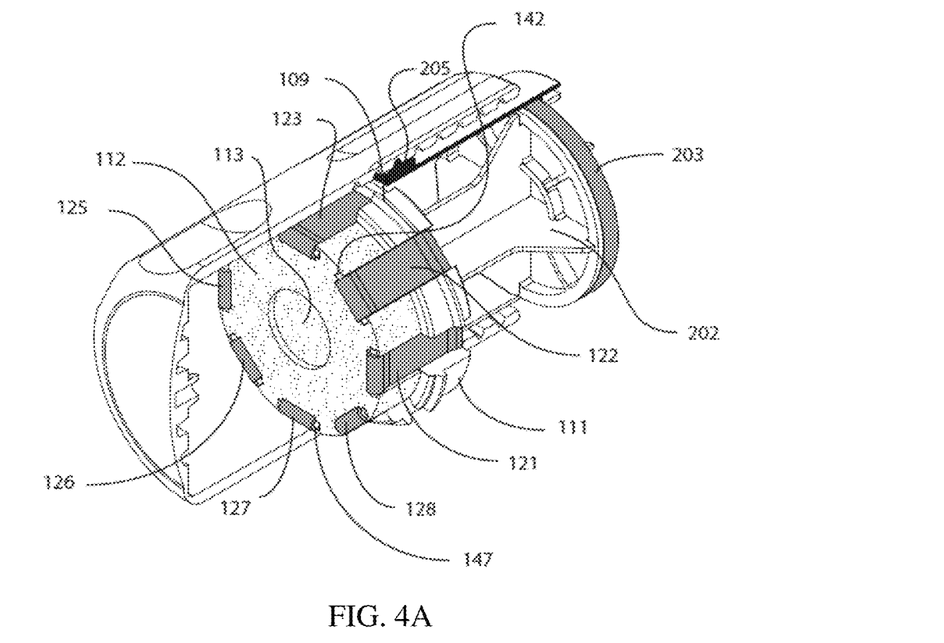
FIG. 4A and FIG. 4B are perspective views of FIG. 1A with cut out sections showing the internal components of both the fluid container and the actuator module being engaged in an operable state, there is no fluid in the fluid container.
Figure 4B:
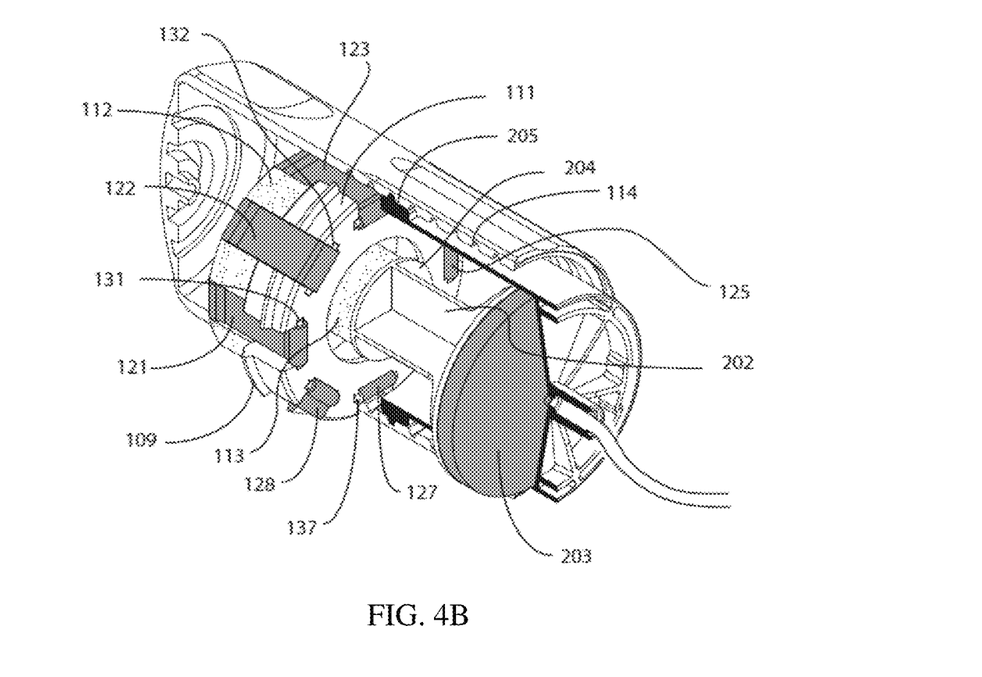

Referring to FIGS. 4A and 4B, the elastic bands are loops that are anchored to the disc plates with pins, for example elastic band 122 looping around pin 132 located on disc plate 111, and pin 142 located in disc plate 112. A similar configuration is provided in elastic band 127 looping around pin 137 located in plate 111 and pin 147 in plate 112. The pins described could be secured to the disc plates by means of interlocking features. It is understandable that other means of securing the elastic bands to the movable discs are covered by the scope of the disclosure.

The structure applied in securing the elastic bands or loops onto the disc plates may take into consideration the extent and number of bands which would be pre stressed by means of shortening its initial length, compared to the length between the points of attachment on both adjacent disc plates.

Figure 5A:
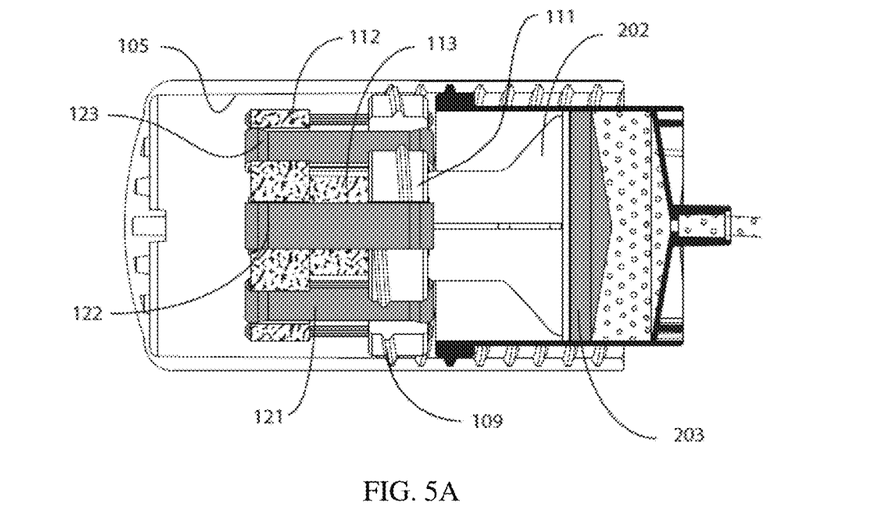
FIG. 5A is a cross sectional view of FIG. 1A showing the fluid container and actuator module in an engaged operable state, the elastic bands are stretched and act as thrusters in pushing the fluid out from the fluid container.
Figure 5B:
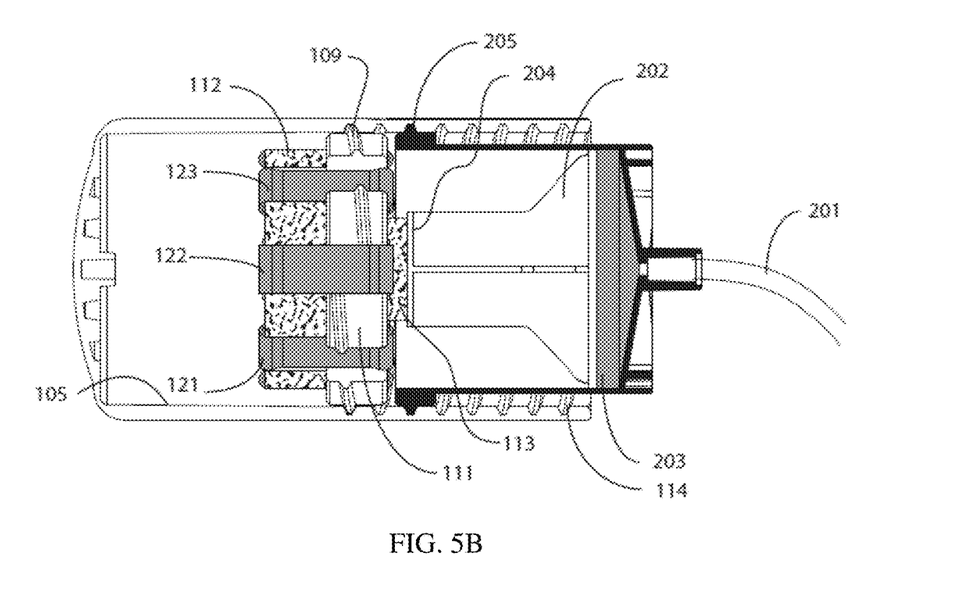
FIG. 5B is another cross sectional view of FIG. 1A showing the device in an operable state, the elastic bands having recoiled to its initial state.

Referring to FIGS. 5A and 5B, the second disc plate 112 moves away and outwards from first disc plate 111, when the elastic bands attached around is the disc plated 111, 112, and are stretched. In this movement of stretching the elastic band, the protrusion 113 will slide axially through the centre opening of the first disc plate 111 which is fixed to housing 120, during the operation of the fluid delivery apparatus. The relative movements of the disc plates 111, 112 is coupled to the fluid container 102 by means of the protrusion 113 and the plunger 202, providing the axial displacement of plunger 202 needed for gasket 203 to push the fluid out from fluid container 102.

As the first disc plate 111 is fixed to housing 120 during the fluid dispensing movements and second disc plate 112 moves relative to first disc plate 111, there is no necessity for the actuator module to recess into the void of the fluid container 102 created by dispensed fluid. This feature simplifies the structure and manufacturing process, and overcomes the disadvantage of devices that utilizes compression force to push liquid out from containers.

Figure 6A:
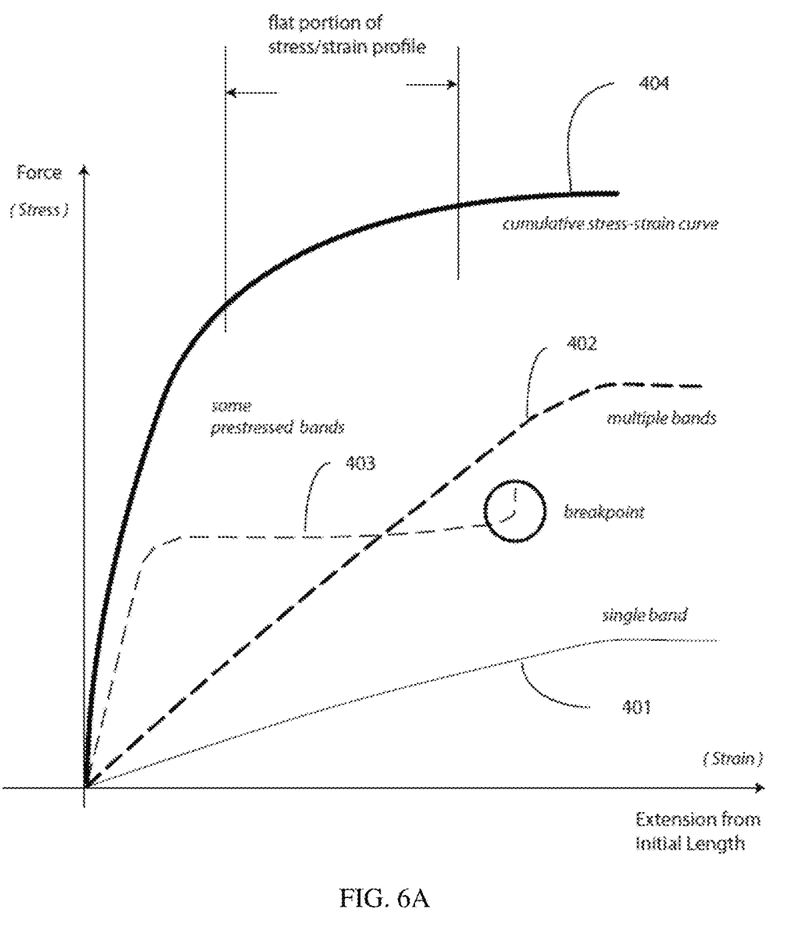
FIGS. 6A and 6B are graphs that approximate the relationship between force exerted by the elastic bands onto the fluid container plunger and the distance displaced from the initial position of the disc plates.

Referring to FIG. 6A, a stress-strain curve of a single elastic band is represented by reference number 401. As multiple elastic bands are secured circumferentially around both disc plates 111 and 112, curve 402 would be typical stress-strain relationship. The pre-stressed elastic bands, for example using loops that have shorter circumference (and lengths when they are flattened) than the distance of the pins around which they looped, will produce a stress-strain curve similar to 403. In one embodiment, all the elastic bands have the same elastic coefficient, but a first group of elastic bands have a first length and a second group of elastic bands have a second length different from the first length. Alternatively, all the elastic bands may have the same length but a first group of the elastic bands have a first elastic coefficient and the second group of elastic bands have a second elastic coefficient different from the first elastic coefficient. Based on a combination of first and second groups of elastic bands with different properties e.g. lengths or elastic coefficient, some pre-stressed and some non pre-stressed elastic bands, or come more pre-stressed and some less pre-stressed elastic bands, the resilient member will perform according to a stress-strain curve similar to 404.

The effect of having a longer disc protrusion 113 as discussed earlier allows the device to operate in the flatter regressive range of the stress-strain curve.

When the fluid delivery apparatus is ready to use, port 140 is opened to remove the resistance to fluid flow, and the elastic bands will then be allowed to shrink, i.e. to release the elastic potential energy stored therein when being stretched. The shrinking of the elastic bands will follow a stress-strain curve 405 shown in FIG. 6B. The slightly regressive curve may be optimized to take into account the slightly higher surface resistance in the fluid container when fluid content is filled at its maximum storage capacity in the fluid container.

Figure 6B:
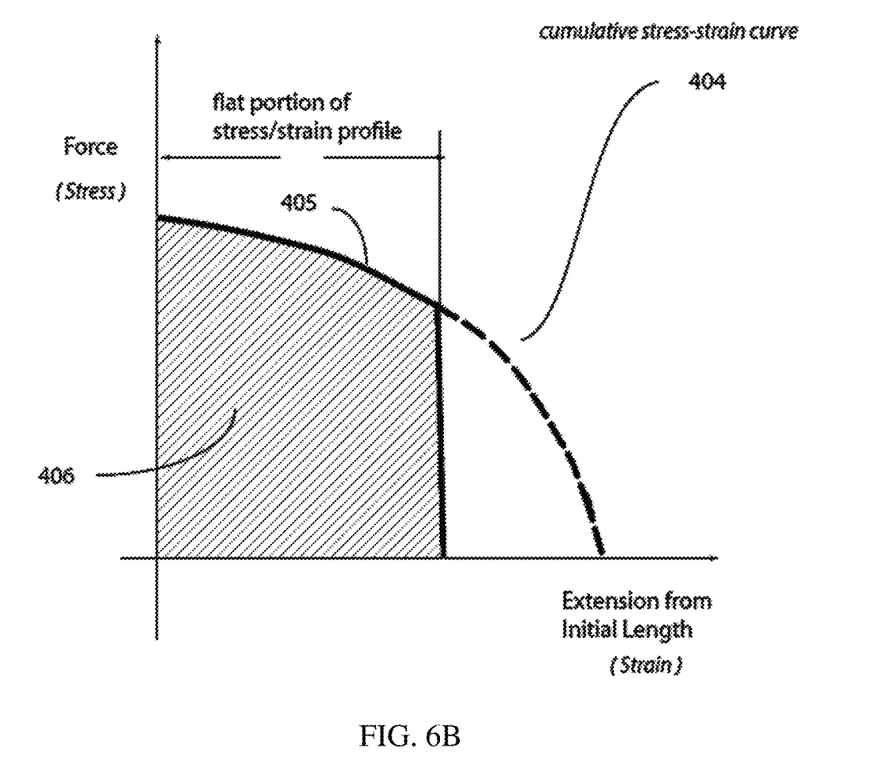

The shaded region 406 represents the elastic potential energy that is transferred into kinetic energy in pushing the plunger which ejects the fluid out of the fluid container.

Figure 7:
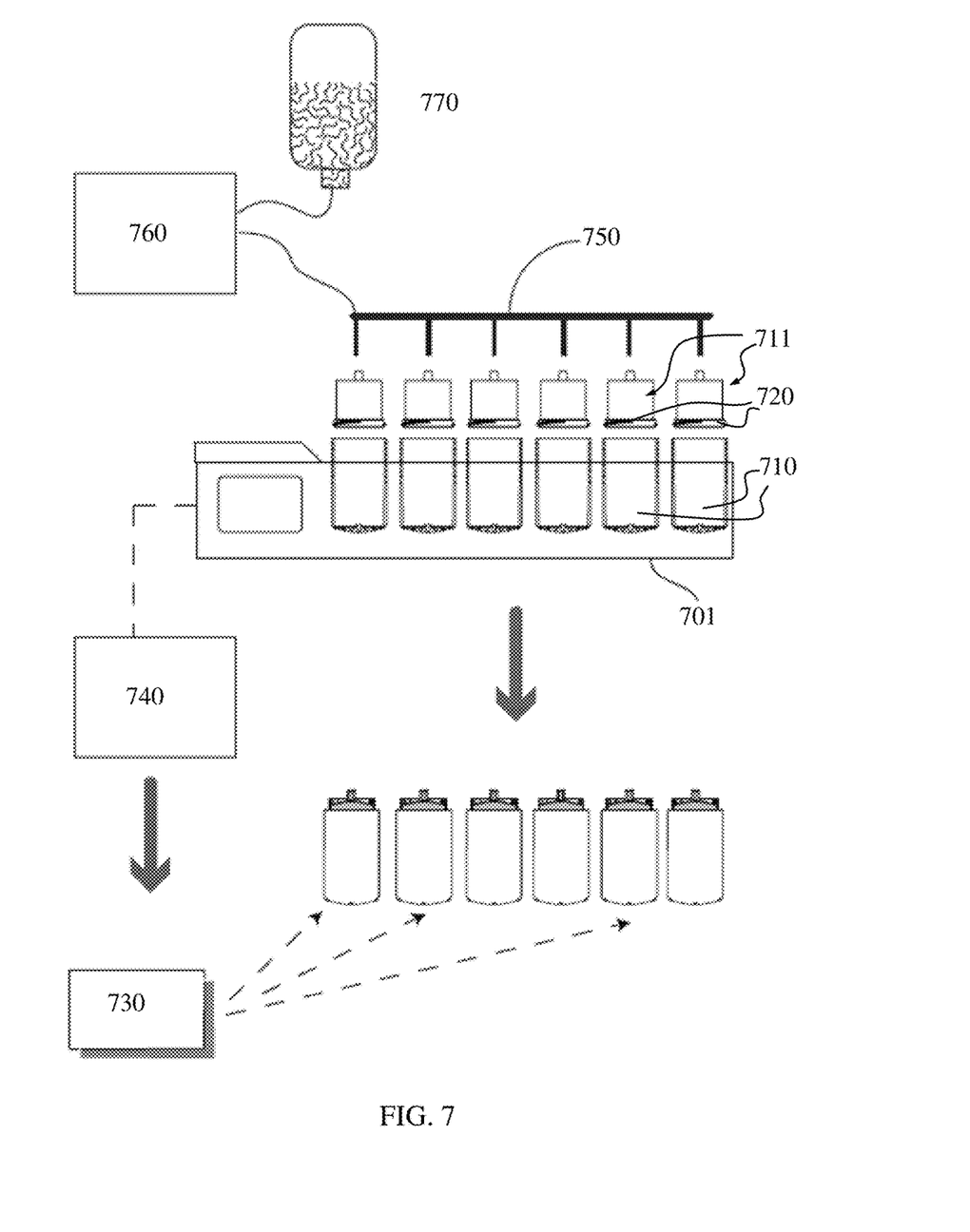
FIG. 7 shows the invention from a systems perspective. The fluid containers and actuator modules are elements of an integrated drug preparation system where the fluid containers are filled, engaged with the actuator modules and labelled with secure positive patient-drug identification.

Referring to FIG. 7, embodiments of the invention is presented from a systems perspective in which the fluid delivery apparatus disclosed forms an integral part of a drug preparation and delivery system. The ability in multiple simultaneous filling of fluid into each fluid delivery apparatus, which is not typically possible in known elastomeric ambulatory pumps, and the ability of presenting the fluid container as a pre fillable device, allowing the fluid delivery apparatus to be used after extended storage without impacting its performance suggest an eco-system evolving from its unique features described above. A system according to an embodiment of the present invention includes auto filling and actuating of multiple devices at an actuator station 701 through a manifold 750 which is connected to a fluid bag 770 through a repeater filling pump 760. Filling the fluid containers would cause the stopper gaskets 720 of each fluid container 710 to move downwards, hence sensors installed in the actuator workstation 701 that spins the actuator module 711 may allow variable fill volume to be programmed. Further, labels 730 with patient and medication data could be generated by printer 740 to ensure positive patient, drug and device identification.

Although embodiments of the present invention have been illustrated in conjunction with the accompanying drawings and described in the foregoing detailed description, it should be appreciated that the present invention is not limited to the embodiments disclosed. Therefore, the present invention should be understood to be capable of numerous rearrangements, modifications, alternatives and substitutions without departing from the spirit of the invention as set forth and recited by the following claims.

We claim:

1. A fluid delivery apparatus comprising:
   a housing;
   a fluid container having a port at one end thereof;
   a plunger movably disposed in the fluid container to form a chamber between the plunger and the port, wherein a fluid is filled into and sealed in the chamber;
   a support member disposed in the housing;
   an actuator movably disposed through the support member, the actuator having a first end disposed at one side of the support member and a second end disposed at an opposite side of the support member;
   a resilient member connecting the support member to the actuator at the second end,
   wherein when the fluid container is attached to the housing, the plunger acts against the first end of the actuator to stretch the resilient member along a longitudinal direction of the housing;
   wherein when the port is opened, the resilient member shrinks to drive the actuator to push the plunger toward the port to eject the fluid out of the chamber from the port,
   and wherein the fluid container is movable relative to the housing towards the resilient member to push the actuator to stretch the resilient member.

2. The apparatus of claim 1, wherein the housing has thread grooves formed at an inner surface thereof, the fluid container has a container flange engageable to the thread groove, wherein rotation of the fluid container causes the fluid container to move relative to the housing along the longitudinal direction toward the resilient member to push the actuator to compress the resilient member.

3. The apparatus of claim 1, wherein the housing has thread grooves formed at an inner surface thereof, wherein the support member has screw threads formed on an external surface thereof, and the support member is movably attached to the housing by the engagement of the screw threads and the thread grooves.

4. The apparatus of claim 3, wherein the screw threads are truncated to form recesses within which the resilient member is disposed.

5. The apparatus of claim 1, wherein the resilient member includes a first group of elastic bands and a second group of elastic bands parallelly connecting the support member to the actuator at the second end.

6. The apparatus of claim 5, wherein the first and second groups of elastic bands are alternately arranged around a circumference of the support member.

7. The apparatus of claim 6, wherein each of the first group of elastic bands has a first length and a first elastic coefficient, each of the second group of elastic bands has a second length and a second elastic coefficient, wherein the second length is the same as the first length, and the second elastic coefficient is different from the first elastic coefficient.

8. The apparatus of claim 6, wherein each of the first group of elastic bands has a first length and a first elastic coefficient, each of the second group of elastic bands has a second length and a second elastic coefficient, wherein the second elastic coefficient is the same as the first elastic coefficient, and the second length is different from the first length.

9. A fluid delivery apparatus comprising:
   a housing;
   a fluid container having a port at one end thereof;
   a plunger movably disposed in the fluid container to form a chamber between the plunger and the port,
   a support member disposed in the housing;
   an actuator movably disposed through the support member, the actuator having a first end disposed at one side of the support member and a second end disposed at an opposite side of the support member;
   a resilient member connecting the support member to the actuator at the second end,
   wherein when a fluid is filled in the chamber and the port closed, and when the fluid container is attached to the housing, the plunger acts against the first end of the actuator to stretch the resilient member along a longitudinal direction of the housing;
   wherein when the port is opened, the resilient member shrinks to drive the actuator to push the plunger toward the port to eject the fluid out of the chamber from the port,
   and wherein the fluid container is movable relative to the housing towards the resilient member to push the actuator to stretch the resilient member.

10. The apparatus of claim 9, wherein the housing has thread grooves formed at an inner surface thereof, the fluid container has a container flange engageable to the thread groove, wherein rotation of the fluid container causes the fluid container to move relative to the housing along the longitudinal direction toward the resilient member to push the actuator to compress the resilient member.

11. The apparatus of claim 9, wherein the housing has thread grooves formed at an inner surface thereof, wherein the support member has screw threads formed on an external surface thereof, and the support member is movably attached to the housing by the engagement of the screw threads and the thread grooves.

12. The apparatus of claim 11, wherein the screw threads are truncated to form recesses within which the resilient member is disposed.

13. The apparatus of claim 9, wherein the resilient member includes a first group of elastic bands and a second group of elastic bands parallelly connecting the support member to the actuator at the second end.

14. The apparatus of claim 13, wherein the first and second groups of elastic bands are alternately arranged around a circumference of the support member.

15. The apparatus of claim 14, wherein each of the first group of elastic bands has a first length and a first elastic coefficient, each of the second group of elastic bands has a second length and a second elastic coefficient, wherein the second length is the same as the first length, and the second elastic coefficient is different from the first elastic coefficient.

16. The apparatus of claim 14, wherein each of the first group of elastic bands has a first length and a first elastic coefficient, each of the second group of elastic bands has a second length and a second elastic coefficient, wherein the second elastic coefficient is the same as the first elastic coefficient, and the second length is different from the first length.

* * * * *